(12) United States Patent
Liu

(10) Patent No.: US 9,839,240 B2
(45) Date of Patent: Dec. 12, 2017

(54) ATOMIZATION APPARATUS, ELECTRONIC CIGARETTE, AND ASSEMBLY METHOD THEREFOR

(71) Applicant: HUIZHOU KIMREE TECHNOLOGY CO., LTD. SHENZHEN BRANCH, Shenzhen, Guangdong (CN)

(72) Inventor: Qiuming Liu, Guangdong (CN)

(73) Assignee: HUIZHOU KIMREE TECHNOLOGY CO., LTD. SHENZHEN BRANCH, Shenzhen (CN)

( * ) Notice: Subject to any disclaimer, the term of this patent is extended or adjusted under 35 U.S.C. 154(b) by 0 days.

(21) Appl. No.: 15/108,328

(22) PCT Filed: Dec. 26, 2013

(86) PCT No.: PCT/CN2013/090596
§ 371 (c)(1),
(2) Date: Jun. 27, 2016

(87) PCT Pub. No.: WO2015/096107
PCT Pub. Date: Jul. 2, 2015

(65) Prior Publication Data
US 2016/0316820 A1 Nov. 3, 2016

(51) Int. Cl.
*A24F 47/00* (2006.01)
*F16J 15/02* (2006.01)
(Continued)

(52) U.S. Cl.
CPC ........... *A24F 47/008* (2013.01); *F16J 15/022* (2013.01); *H05B 3/04* (2013.01); *H05B 3/26* (2013.01);
(Continued)

(58) Field of Classification Search
CPC .............................. A24F 47/008; A61M 15/06
See application file for complete search history.

(56) References Cited

U.S. PATENT DOCUMENTS

| 9,700,075 B2 * | 7/2017 | Liu | A24F 47/008 |
| 2013/0319407 A1 * | 12/2013 | Liu | A61M 15/06 |
| | | | 128/202.21 |
| 2016/0316820 A1 * | 11/2016 | Liu | A24F 47/008 |

FOREIGN PATENT DOCUMENTS

CN 203243942 U 10/2013

OTHER PUBLICATIONS

International Search Report of PCT Patent Application No. PCT/CN2013/090596 dated Sep. 29, 2014.

* cited by examiner

*Primary Examiner* — James Harvey

(57) ABSTRACT

An atomization assembly configured to be combined with a battery assembly to form an electronic cigarette comprises a mouthpiece and a body detachable with the mouthpiece. The body includes an open end to discharge smoke into the mouthpiece, an oil storage cavity for storing tobacco oil is defined inside the body, a receiving groove is defined at the open end, an filler hole connected to the oil storage cavity is defined on a bottom wall of the receiving groove, and an elastomeric seal for sealing up the filler hole is received in the receiving groove. By implementing the filler hole, it is easier to add the tobacco oil, and by implementing the elastomeric seal, the tobacco oil can be avoided leaking out. Further, the atomization assembly is provided with simple structure, compact connection and easy assembly.

19 Claims, 8 Drawing Sheets

(51) Int. Cl.
   *H05B 3/26*     (2006.01)
   *H05B 3/04*     (2006.01)
   *H05B 3/44*     (2006.01)
   *A61M 15/06*    (2006.01)
(52) U.S. Cl.
   CPC ............... *H05B 3/44* (2013.01); *A61M 15/06* (2013.01); *H05B 2203/014* (2013.01); *H05B 2203/021* (2013.01); *H05B 2203/022* (2013.01)

ATOMIZATION APPARATUS, ELECTRONIC CIGARETTE, AND ASSEMBLY METHOD THEREFOR

TECHNICAL FIELD

The present application relates to the field of electronic products, and more particularly to an atomization assembly, an electronic cigarette and a method for assembling the electronic cigarette.

BACKGROUND

Generally, an electronic cigarette consists of an atomization assembly and a battery assembly, the atomization assembly is configured to atomize the tobacco oil and produce smoke for smoking, and the battery assembly is configured to provide electricity supply for the atomization assembly. As shown in FIG. 1, in the prior art, a body 3 of the atomization assembly of the electronic cigarette is connected to a mouthpiece 1 by the connection between a first metal thread portion 111 and a second metal screw 112, the first metal screw 111 is connected to the mouthpiece 1 with an interference fit, and the second metal screw 112 sheathes the body 3. In the prior art, an extension tube 114 extends from one end of the mouthpiece 1, and the end of the mouthpiece 1 sheathes the first metal threaded portion 111. The extension tube 114 is inserted into the body 3, to ensure that an air flow path defined in the mouthpiece 1 and an oil storage cavity 33 defined in the body are isolated from one another.

However, when adding the tobacco oil, after removing the mouthpiece 1 from the body 3, the tobacco oil should be carefully added along the side wall of the body 3. If too much tobacco oil is added or a shock occurs when adding the tobacco oil, it is easy to lead the tobacco oil leaking out via a smoke flow path 113 of the body 3. Meanwhile, the mouthpiece 1 is easy to be contaminated with the tobacco oil when the mouthpiece 1 is inserted into the body 3, and the tobacco oil is easy to be leaked out to the smoke flow path 113 via the abutting position between the extension tube 114 and the body 3, so that it is easy for smokers to suck the tobacco oil and the taste of smoking will be affected. Moreover, it is easy for the tobacco oil to leak out to the outside of the atomization assembly via the connection between the first metal threaded portion 111 and the second metal threaded portion 112.

In conclusion, it is inconvenient for the atomization assembly to add the tobacco oil, and it is easy for the tobacco oil to leak out to the smoke flow path 113 and the outside of the atomization assembly. So the atomization assembly in the prior art needs to be improved.

BRIEF SUMMARY

Aiming at the drawbacks in the prior art that it is inconvenient for the atomization assembly to add the tobacco oil and it is easily to cause the leakage of the tobacco oil, the objective of the present application is to provide an atomization assembly configured to be combined with a battery assembly to form an electronic cigarette, comprising a mouthpiece and a body detachable with the mouthpiece, the body includes an open end that is configured to discharge smoke into the mouthpiece, an oil storage cavity configured to store tobacco oil is defined inside the body, a receiving groove is defined at the open end, an filler hole connected to the oil storage cavity is defined on a bottom wall of the receiving groove, and an elastomeric seal configured to seal up the filler hole is received in the receiving groove.

In the atomization assembly of the present application, the elastomeric seal is inserted into the filler hole and is elastically abutted against an inner wall of the filler hole.

In the atomization assembly of the present application, one end of the elastomeric seal is abutted against the receiving groove, and the other end of the elastomeric seal is abutted against the mouthpiece.

In the atomization assembly of the present application, the elastomeric seal includes a through hole that is configured to discharge the smoke into the mouthpiece.

In the atomization assembly of the present application, a first convex abutted against a side wall of the receiving groove is defined outwardly on an outer wall of the elastomeric seal and in a radial direction of the elastomeric seal.

In the atomization assembly of the present application, a receiving cavity configured to accommodate an atomization unit is formed inside the body, the atomization unit is configured to atomize the tobacco oil stored in the oil storage cavity and produce the smoke, a connection tube extends from the bottom wall of the receiving groove to the inside the receiving cavity and is configured to guide the smoke flowing to the through hole, and the connection tube is connected to the through hole.

In the atomization assembly of the present application, one end of the connection tube, away from the atomization unit, extends to the inside the receiving groove, an inner cavity configured to accommodate a part of the connection tube is defined inside the elastomeric seal, and the inner cavity is connected to the through hole.

In the atomization assembly of the present application, a second convex abutted against a side wall of the connection tube is defined inwardly on a side wall of the inner cavity and in a radial direction of the inner cavity.

In the atomization assembly of the present application, a fixed tube configured to receive the atomization unit is defined at one end of the connection tube, the end of the connection tube is away from the open end; a first connector is defined at one end of the fixed tube, the end of the fixed tube is away from the connection tube, the first connector is configured to avoid the tobacco oil leaking to the outside of the body, an outer wall of the first connector abuts against the inner wall of the body, and the outer wall of the fixed tube, the inner wall of the body and the first connector are enclosed to form the oil storage cavity.

In the atomization assembly of the present application, an oil outlet is defined on the side wall of the fixed tube that is close to a bottom of the oil storage cavity, and the oil outlet is configured to guide the tobacco oil stored in the oil storage cavity flowing to the atomization unit.

In the atomization assembly of the present application, a connection sleeve is arranged between the fixed tube and the connection tube, and the connection sleeve is configured to avoid the tobacco oil permeating to the connection tube.

In the atomization assembly of the present application, the connection sleeve, the connection tube and the fixed tube are coaxially arranged, and a first slot into which the fixed tube is inserted is defined in the connection sleeve.

In the atomization assembly of the present application, a second slot is configured to accommodate and abut against the connection tube is defined in the connection sleeve, and the connection tube, the connection sleeve and the fixed tube are axially connected to each other.

In the atomization assembly of the present application, a third convex abutted against the connection tube is defined inwardly on the inner wall of the second slot and in a radial direction of the second slot.

In the atomization assembly of the present application, the open end includes a first threaded portion that is integrated with the body, and a second threaded portion adapted to the first threaded portion is defined at one end of the mouthpiece, the end of the threaded portion is close to the open end, and the mouthpiece is detachably connected to the body via the connection between the first threaded portion and the second threaded portion.

In the atomization assembly of the present application, the first threaded portion comprises a connection part and a first thread defined on an outer peripheral surface of the connection part, and the connection part is formed by reducing a diameter of the open end by the body; and the second threaded portion comprises a second thread, the second thread is defined on an inner peripheral surface of the mouthpiece and is adapted to the first thread.

In the atomization assembly of the present application, a fourth convex abutted against the second thread is defined at one end of the elastomeric seal and the end of the elastomeric seal is close to the mouthpiece.

In another aspect, this present application further provides an electronic cigarette comprising an atomization assembly and a battery assembly configured to provide electricity supply for the atomization assembly, the atomization assembly is abovementioned atomization assembly.

In yet another aspect, this present application further provides a method for assembling an electronic cigarette, the electronic cigarette comprises an atomization assembly and a battery assembly, the atomization assembly is abovementioned atomization assembly, and the method comprises the following steps:

a. a step for adding the tobacco oil: adding the tobacco oil to the oil storage cavity via the filler hole that is defined on the bottom wall of the receiving groove;

b. a step for sealing: inserting the elastomeric seal into the receiving groove to seal up the filler hole;

c. a step for electrical connecting: connecting the atomization assembly to the battery assembly, and making the atomization assembly be electrical connected to the battery assembly.

By implementing the atomization assembly, the electronic cigarette and the method for assembling the electronic cigarette, the following advantages can be achieved: by means of arranging a receiving groove at the open end of the body, and defining the filler hole connected to the oil storage cavity on the bottom wall of the receiving groove, the tobacco oil can be firstly added to the oil storage cavity via the filler hole directly by just removing the mouthpiece from the open end when adding the tobacco oil, and the tobacco oil will not be leaked out in the process of adding the tobacco oil; and then the filler hole can be sealed up by the elastomeric seal after the tobacco oil is added; Lastly, the mouthpiece is assembled to the open end to avoid being contaminated with the tobacco oil. Accordingly, it is much cleaner. Meanwhile, as the filler hole is always sealed up by the elastomeric seal during using, it is able to effectively prevent the tobacco oil between the oil storage cavity and the mouthpiece from leaking out.

Further, the mouthpiece and the body of the atomization assembly are connected by means of a screw connection between a first threaded portion defined on the body and a second thread defined on the mouthpiece, so as to reduce the number of the parts and hence lead to cost saving and assembling efficiency increasing.

Furthermore, in the atomization assembly, the electronic cigarette and the method for assembling the electronic cigarette of the present embodiment, there is no need to arrange an extension tube provided in the prior art in the mouthpiece, and the oil storage cavity can be filled up so as to increase the reserves of the tobacco oil and it hence improves convenience in refueling and improves user experiences.

BRIEF DESCRIPTION OF THE DRAWINGS

The present application will be further described with reference to the accompanying drawings and embodiments in the following, in the accompanying drawings.

DETAILED DESCRIPTION OF THE PREFERRED EMBODIMENT

Figure 1:
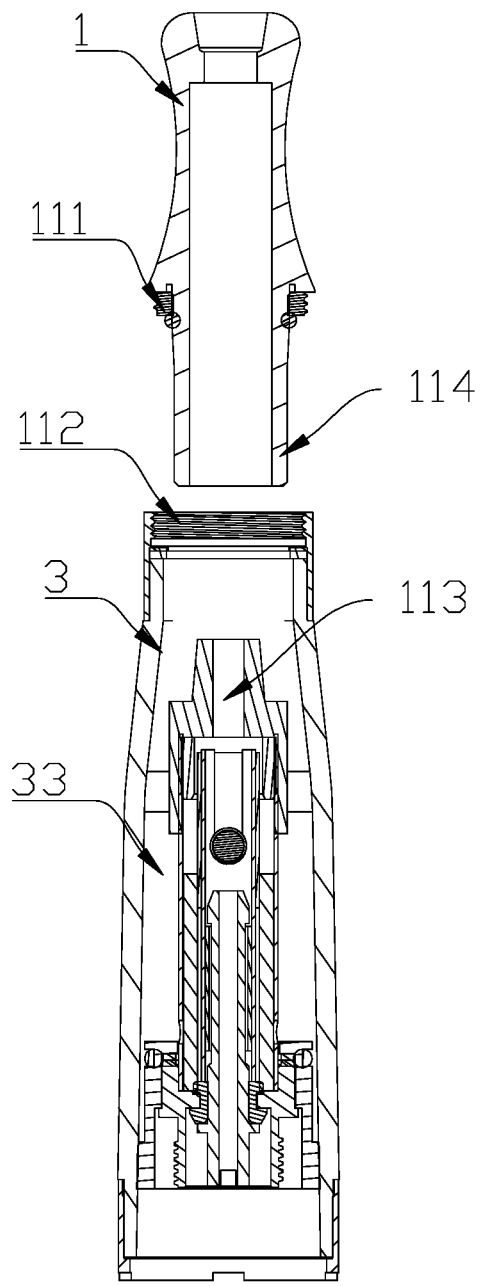
FIG. 1 is a schematic view of an atomization assembly in the prior art.
Figure 2:
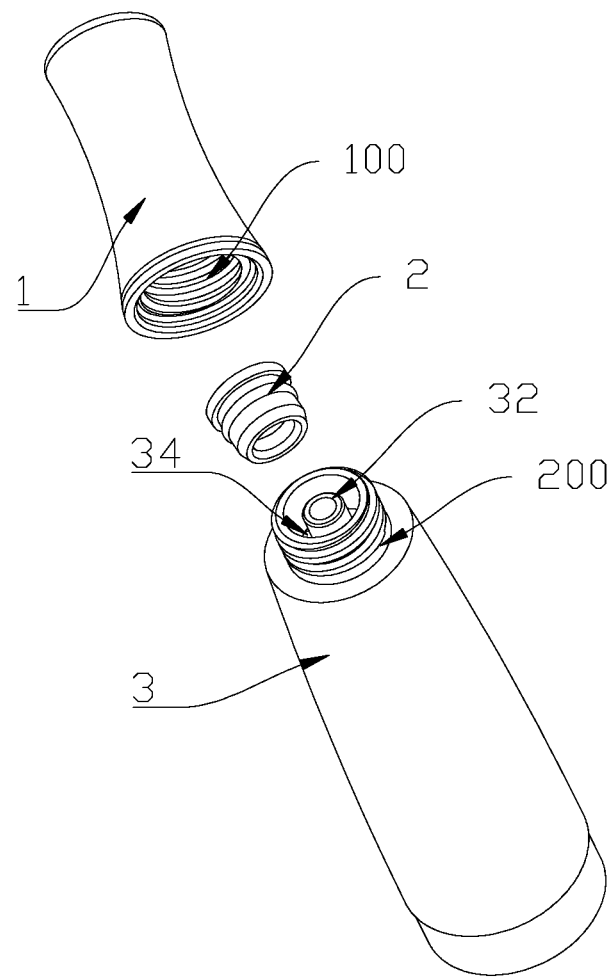
FIG. 2 is a schematic view of an atomization assembly of a preferred embodiment of the present application.
Figure 3:
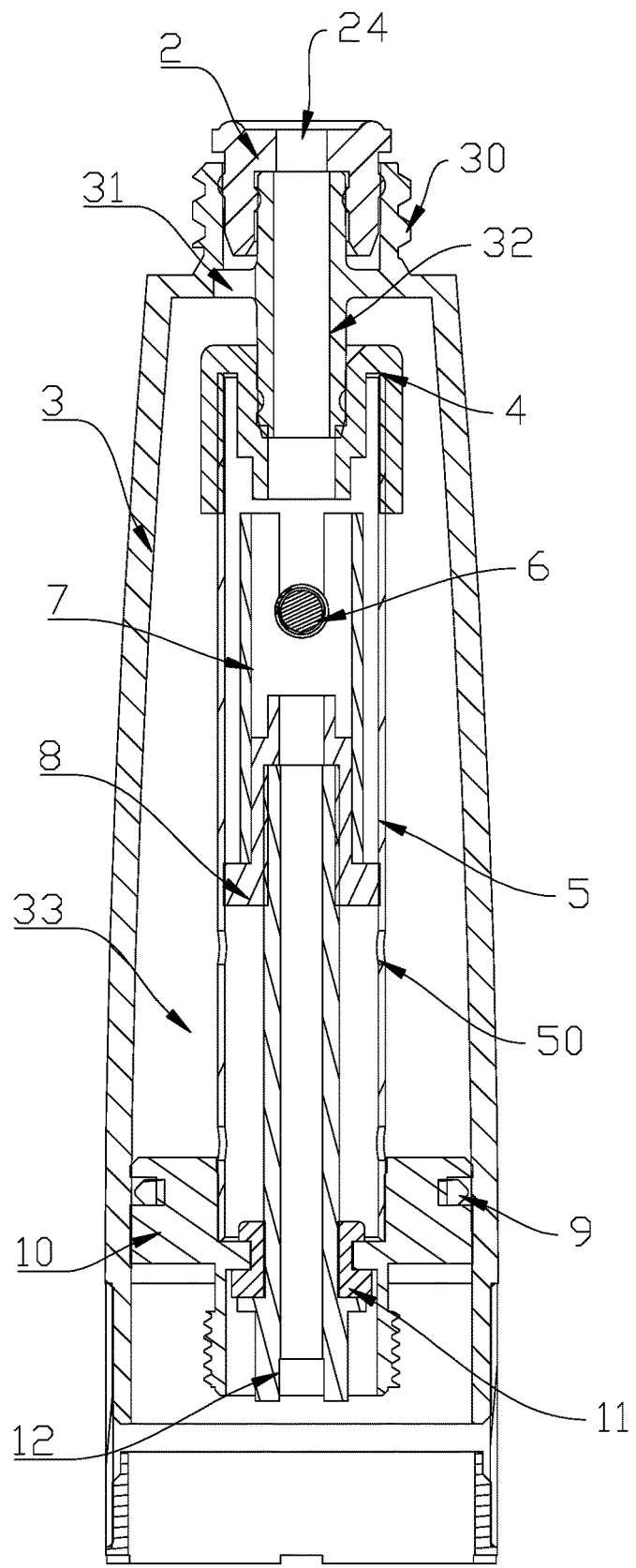
FIG. 3 is a sectional view of the atomization assembly shown in FIG. 2.

In order to solve the problem in the prior art as shown in FIG. 1, that the connection structure between the mouthpiece 1 and the body 3 is complicated, it is inconvenient to add the tobacco oil, and it is easy for the tobacco oil to leak out via the connection between the mouthpiece 1 and the oil storage cavity 33, the innovation point of the present invention is to provide an atomization assembly as shown in FIG. 2. The atomization assembly comprises a mouthpiece 1 and a body 3 detachable with the mouthpiece 1. Smoke produced by atomizing tobacco oil flows from an open end 30 of the body 3 to the mouthpiece 1. Referring to FIG. 3, a filler hole 31 is defined at the open end 30 axially. The filler hole 31 is connected to an oil storage cavity 33. Meanwhile, an elastomeric seal 2 is mounted on the open end 30 for sealing up the filler hole 31. Therefore, the open end 30 in the present invention includes a receiving groove 34 that is configured to accommodate the elastomeric seal 2. The receiving groove 34 forms a bottom wall in the open end. The filler hole 31 is defined on the bottom wall of the receiving groove 34. Because the filler hole 31 is defined on the bottom wall of the receiving groove 34, it only needs to inject the tobacco oil from the filler hole 31 when adding the tobacco oil. Further, using the elastomeric seal 2 to seal up the filler hole 31 after the tobacco oil is added can effectively avoid the tobacco oil leaking out to the mouthpiece 1. In this way, the defects in the prior art can be solved, and the defects are that it is inconvenient to add the tobacco oil for the atomization assembly and it is easy to cause the tobacco oil leaking out via the connection between the mouthpiece 1 and the oil storage cavity 33. Furthermore, in the present application, the oil storage cavity 33 extends to the connection between the mouthpiece 1 and the body 3, and hence it is able to overcome the defect that the space of the oil storage cavity 33 is reduced by an extension tube 114 defined on the mouthpiece 1 and needed to be inserted into the atomizer assembling body 3 in the prior art.

In order to explain the purpose, the technical features, and the effect of the present application more clearly, the specific embodiments of the present application will be described in detail referring to the drawings.

In the present application, the atomization assembly is configured to be combined with a battery assembly to form an electronic cigarette. In the embodiment as shown in FIG. 2, the atomization assembly comprises a mouthpiece 1 and a body 3, and the mouthpiece 1 is detachable with the body 3 in the present embodiment. The body 3 includes an oil storage cavity (not shown in FIG. 2) that is configured to store tobacco oil. An open end 30 of the body 3 is approximately in a sealed columnar structure. The open end 30 includes a smoke flow path, and the smoke flow path axially runs through the open end 30 and discharges the smoke into the mouthpiece 1. Meanwhile, the open end 30 includes a filler hole 31, and the filler hole 31 axially runs through the open end 30 and is isolated from the smoke flow path. An elastomeric seal 2 is received in the open end 30 in the present embodiment to seal up the filler hole 31, so a receiving groove 34 is defined in the open end 30 to receive the elastomeric seal 2. The receiving groove 34 forms a bottom wall in the open end 30, wherein, the receiving groove 34 may be concave, arched, semicircular or annular and the like, which is not limited here. Referring to FIG. 3, the filler hole 31 is defined on the bottom wall of the receiving groove 34 and is connected to the oil storage cavity 33. When the oil storage cavity 33 is short for tobacco oil, it is able to add the tobacco oil into the oil storage cavity 33 via the filler hole 31. Meanwhile, the elastomeric seal 2 is also received in the receiving groove 34 in the present embodiment to seal up the filler hole 31. Removing the elastomeric seal 2 from the receiving groove 34 when it is need to add the tobacco oil, and inserting the elastomeric seal 2 into the receiving groove 34 for sealing up the filler hole 31 after the tobacco oil is added, can effectively avoid the tobacco oil leaking out via the filler hole 31. The smoke produced in the body 3 flows to the mouthpiece 1 via the open end 30. The mouthpiece 1 is contactless with the oil storage 33 that is configured to store the tobacco oil of the body 3, so as to avoid the tobacco oil leaking out via the connection between the oil storage cavity 33 and the mouthpiece 1 during using.

Referring to FIG. 2, in the present embodiment, the open end 30 of the body 3 includes a first threaded portion 200 that is integrated with the body 3. A second threaded portion 100 adapted to the first threaded portion 200 is defined at one end of the mouthpiece 1 and the end of the mouthpiece 1 is closed to the body 3. When using the atomization assembly as shown in FIG. 2, the mouthpiece 1 is screwed to the open end 30 of the body 3 by a screwed connection between the first threaded portion 200 integrated with one of the body 3 and the second threaded portion 100 defined on an inner surface of the mouthpiece 1, thus the mouthpiece 1 is detachably connected to the body 3.

Referring to FIG. 3, in the present embodiment, the first threaded portion 200 includes a connection part and a first thread defined on the outer peripheral surface of the connection part, and the connection part is formed by reducing the diameter of the open end 30 of the body 3 by the body 3. The second threaded portion 100 includes a second thread adapted to the first thread and defined on an inner peripheral surface of the mouthpiece 1. The number of parts of the atomization assembly in the present embodiment is reduced by means of defining the threads in the inner surface of the mouthpiece 1 and in one end of the body 3, and it hence leads to easy assembly and disassembly and firm connection.

Figure 4:
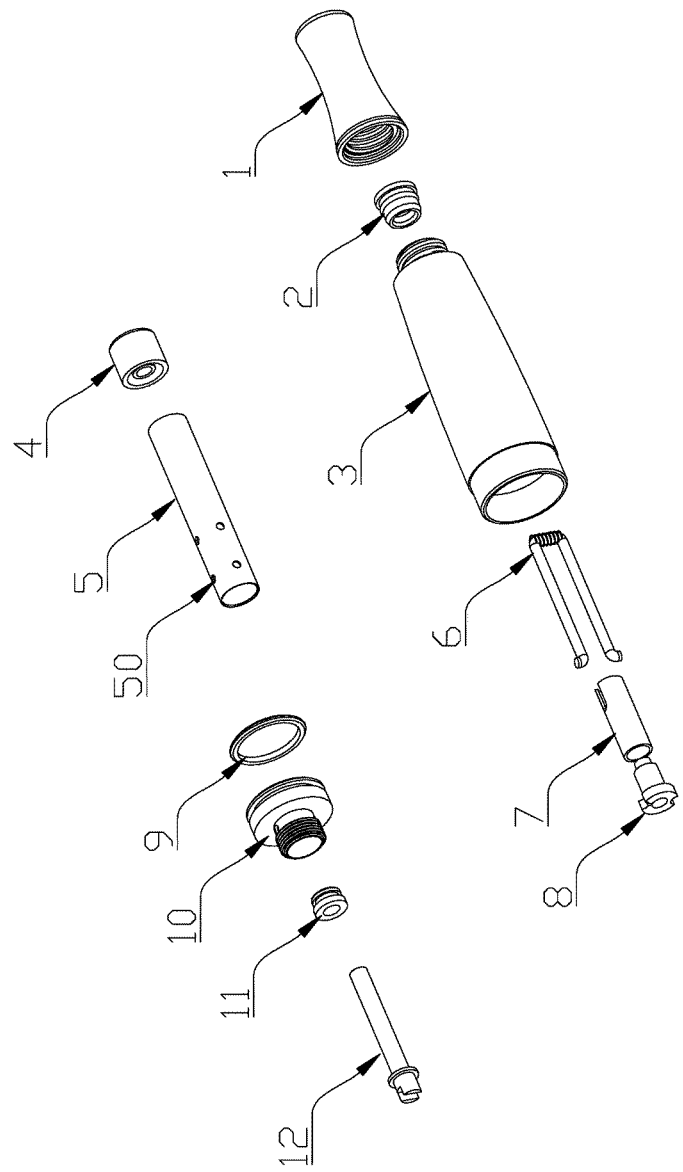
FIG. 4 is an exploded view of the atomization assembly shown in FIG. 2.

Referring to FIGS. 3-4, one end of the elastomeric seal 2 in the present embodiment abuts against the receiving groove 34, and the other end of the elastomeric seal 2 abuts against the mouthpiece 1. Due to the threaded connection between the mouthpiece 1 and the body 3, the mouthpiece 1 and the body 3 keep relatively fixed, thus the elastomeric seal 2 always keeps on sealing up the filler hole 31 during using, so as to avoid the tobacco oil leaking out to the mouthpiece 1 via the filler hole 31.

A receiving cavity (not shown) configured to accommodate an atomization unit is formed inside the body 3. The atomization unit is configured to heat and atomize the tobacco oil in the oil storage cavity 33 to produce smoke. The elastomeric seal 2 in the present embodiment is a seal cover that is made of silicone gel, and the seal cover is inserted into the open end 30 and is covered on an end face of the open end 30. It should be understand that the elastomeric seal 2 may be made of foam and the like, the material and the shape of the elastomeric seal 2 are not limited here. In order to ensure the smoke can smoothly flow to the mouthpiece 1, a through hole 24 is defined axially in the elastomeric seal 2 in order to guide the smoke to the mouthpiece 1.

Figure 5:
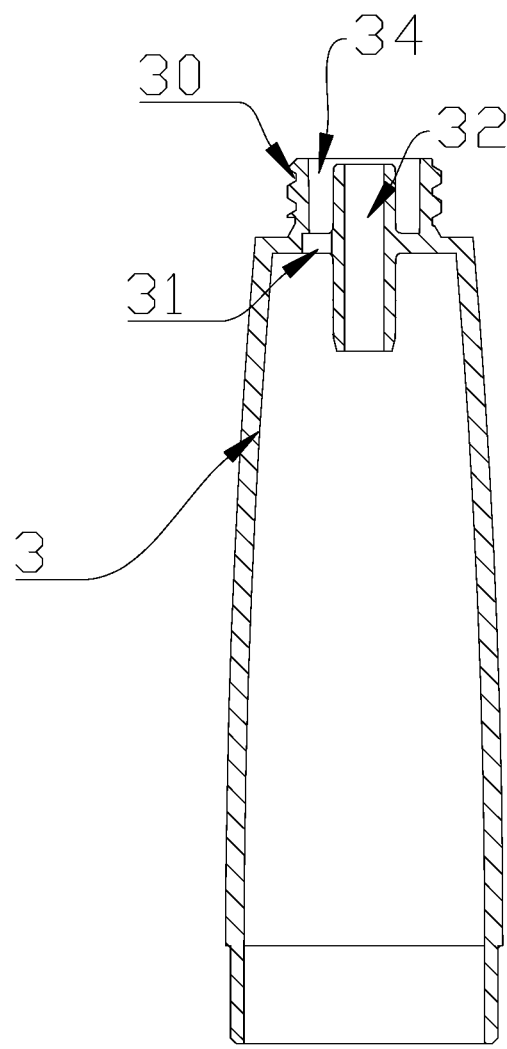
FIG. 5 is a sectional view of a body of the atomization assembly shown in FIG. 2.
Figure 6:
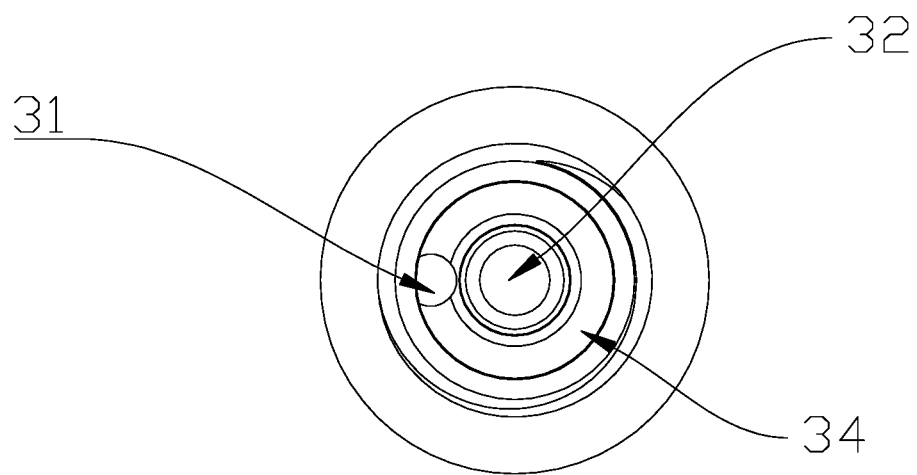
FIG. 6 is a top view of the body shown in FIG. 5.
Figure 7:
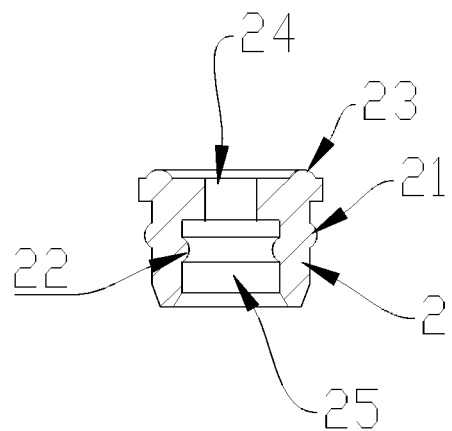
FIG. 7 is a sectional view of an elastomeric seal of the atomization assembly shown in FIG. 3.
Figure 8:
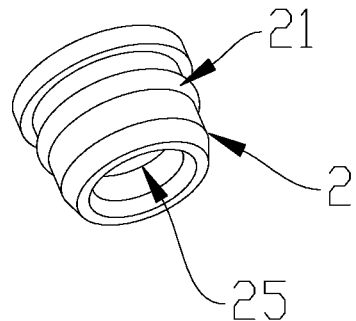
FIG. 8 is a perspective view of a seal cover shown in FIG. 7.

Referring to FIG. 5, a connection tube 32 extends from the bottom wall of the receiving groove 34 to the inside the storage cavity and is configured to guide the smoke flowing to the through hole 24. Combined with FIG. 3, it can be seen that the connection tube 32 is connected to the through hole 24. In order to avoid that the tobacco oil overflows from the filler hole 31 and flows to the storage cavity of the body 3 via the connection tube 32 when too much tobacco oil is added, one end of the elastomeric seal 2, away from the atomization unit, extends to the inside the receiving groove 34 along a direction pointing to the elastomeric seal 2. Referring to FIGS. 7-8, an inner cavity 25 adapted to the connection tube 32 is defined inside the elastomeric seal 2, and the connection tube 32 partially extends to the receiving groove 34 and is accommodated inside the inner cavity 25. The inner cavity 25 is connected to the through hole 24 in order to make sure that the smoke can smoothly flow to the mouthpiece 1 via the elastomeric seal 2.

Referring to FIG. 7 and FIG. 8, the elastomeric seal 2 is approximately semi-closed and is in a hollow cylindrical shape. A first convex 21 abutted against the receiving groove 34 is defined outwardly on the outer wall of the elastomeric seal 2, and the first convex 21 runs in a radial direction of the elastomeric seal 2. A second convex 22 abutted against the connection tube 32 is defined inwardly on the inner wall of the elastomeric seal 2, and the second convex 22 runs in a radial direction of the elastomeric seal 2. The first convex 21 and the second convex 22 are elastic since the elastomeric seal 2 is a cylindrical silicone gel cover. Therefore, the first convex 21 and the second convex 22 can make sure that the elastomeric seal 2 is firmly fastened with the receiving groove 34 and the connection tube 32 on the premise that the elastomeric seal 2 can smoothly remove from the open end 30. In the same way, a fourth convex 23 abutted against the second threaded portion 100 is defined on the surface of the top end of the elastomeric seal 2 in order to obtain a better sealing effect.

It is understandable that the elastomeric seal 2 in the present application is not limited to the above structure as shown in FIGS. 7-8. In the other preferred embodiment, the elastomeric seal 2 may be in a shape that is matched with the filler hole 31, and the elastomeric seal 2 is inserted into the filler hole 31 to seal up the filler hole 31. Further, the elastomeric seal 2 is elastically abutted against the inner surface of the filler hole 31 so that the tobacco oil will not be leaked out and the elastomeric seal 2 can be removed smoothly.

Referring to FIG. 3, in order to make sure that the atomization unit inside the body 3 is relatively fixed, a fixed tube 5 configured to accommodate the atomization unit is defined at one end of the connection tube 32, wherein the end of the connection tube 32 is away from the receiving groove 34 and the connection tube 32 is inside the body 3. A first connector 10 is defined at one end of the fixed tube 5, wherein the end of the fixed tube 5 is away from the connection tube 32. The first connector 10 is configured to fix the fixed tube 5 and avoid the tobacco oil permeating to the outside of the body 3. Referring to FIG. 3, the first connector 10 is embodied in one end of the body 3, wherein the end of the body 3 is away from the open end 3. The inner wall of the first connector 10 abuts against the outer wall of the fixed tube 5. The fixed tube 5, the first connector 10 and the body 3 are coaxially arranged. The outer wall of the fixed tube 5, the inner wall of the body 3 and the first connector 10 are enclosed to form the oil storage cavity 33. The fixed tube 5 is in a hollow structure, and the receiving cavity for accommodating the atomization unit is defined inside the fixed tube 5. An oil outlet 50 is defined on the side wall of the fixed tube 5, the tobacco oil stored in the oil storage cavity 33 flows and permeates into the receiving cavity via the oil outlet 50, and the atomization unit is configured to atomize the tobacco oil in the receiving cavity.

In order to reduce the number of the parts and simplify the assembly processes, the fixed tube 5 and the first connector 10 are all made of conductive materials in the present embodiment. As a result, the first connector 10 is not only configured to fix the fixed tube 5 and to seal up the tobacco oil, but also configured to be electrically connected to a battery assembly. Meanwhile, the fixed tube 5 contacts with the first connector 10 directly, so that the atomization unit inside the fixed tube 5 is electrically connected to the first connector 10 via the direct contact between the atomization unit and the fixed tube 5, and then the atomization unit is electrically connected to the battery assembly. In the present embodiment, an annular groove is defined inwardly on the side wall of the first connector 10 by reducing the diameter of the first connector 10, and the annular groove is arranged coaxially with the first connector 10. A sealing ring 9 is arranged inside the annular groove. Two opposite sides of the sealing ring 9 are abutted against the inner surface of the body 3 and the first connector 10 respectively, so as to ensure that the first connector 10 is fixed in the body 3 and the connection between the first connector 10 and the body 3 is sealed up.

Figure 9:
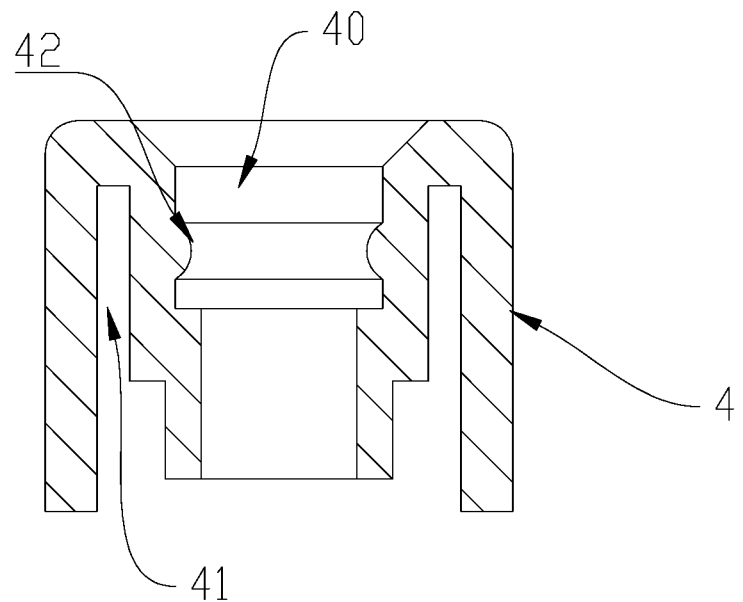
FIG. 9 is a sectional view of a connection sleeve of the atomization assembly shown in FIG. 3.

Referring to FIG. 3, a connection sleeve 4 is coaxially arranged between the fixed tube 5 and the connection tube 32, and the connection sleeve 4 is configured to avoid the tobacco oil permeating to the receiving cavity from the gap between the fixed tube 5 and the connection tube 32 to affect the taste of smoking. And the connection sleeve 4, the fixed tube 5 and the connection tube 32 are coaxially arranged. Referring to FIG. 9, a first slot 41 into which the fixed tube 5 is inserted is defined in the connection sleeve 4. A second slot 40 into which the connection tube 32 is inserted is defined in the connection sleeve 4. A third convex 42 abutted against the connection tube 32 is defined inwardly on the inner wall of the second slot 40, and the third convex 42 runs in a radial direction of the second slot 40. The connection sleeve 4 is made of elastic materials, so the third convex 42 is configured to ensure the connection tube 32 and the connection sleeve 4 are relatively fixed to each other. The connection sleeve 4, the fixed tube 5 and the connection tube 32 are axially connected to each other.

In the present embodiment, the connection tube 32 is integrated with the body 3, so it is more convenient for assembling and it can avoid the tobacco oil or the smoke leaking out from the gaps between the multiple parts.

Figure 10:
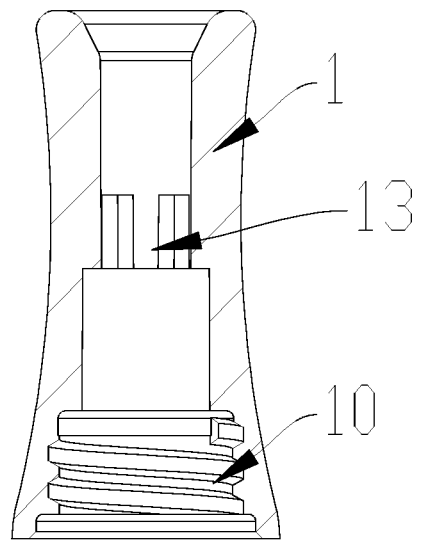
FIG. 10 is a sectional view of a mouthpiece of the atomization assembly shown in FIG. 3.
Figure 11:
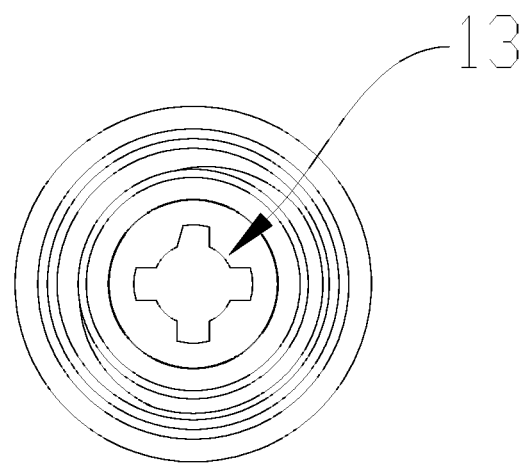
FIG. 11 is a bottom view of the mouthpiece shown in FIG. 10.

Referring to FIGS. 10-11, a second thread is defined at one end of the mouthpiece 1, wherein the end of the mouthpiece 1 is connected to the body 3. The mouthpiece 1 is in a hollow structure. In order to overcome the defects that the taste of smoking is affected due to too much smoke produced, a transition 13 is defined inwardly on the inner surface of the mouthpiece 1. An aperture of a section of the transition 13 is smaller than that of the mouthpiece 1 that is positioned at the two ends of the transition 13.

The structure of the above atomization unit configured to atomize the tobacco oil in the oil storage cavity 33 is prior art. The specific embodiments of the atomization unit will be described in detail as follows. It will be understood that the atomization unit in the present application are not limited to the following embodiments.

Referring to FIGS. 3-4, the first connector 10 is coaxially arranged with the fixed tube 5 in the present embodiment, and the first connector 10 and the fixed tube 5 are all made of conductive materials. Therefore, in the present embodiment, after the atomization assembly is assembled with the battery assembly, the fixed tube 5 is electrically connected to the positive electrode or the negative electrode of the battery assembly via the first connector 10 directly. In order to make the atomization assembly electrically connected to the negative electrode or the positive electrode of the battery assembly, a second connector 12 electrically connected to the battery assembly in the present embodiment is also inserted to the inside the first connector 10. An insulation part 11 is coaxially arranged between the first connector 10 and the second connector 12, to ensure the first connector 10 and the second connector 12 are insulated from each other. In the present embodiment, the atomization unit comprises a heating element 6 configured to heat the tobacco oil, a snorkel 7 configured to make the heating element 6 fixed and an atomization base 8 configured to fix the snorkel 7. A smoke flow path to flow the smoke is formed in the snorkel 7. The atomization base 8 in the present embodiment is coaxially arranged at one end of the second connector 12, wherein the end of the second connector 12 is away from the first connector 10. The snorkel 7 is arranged on the atomization base 8.

Figure 12:
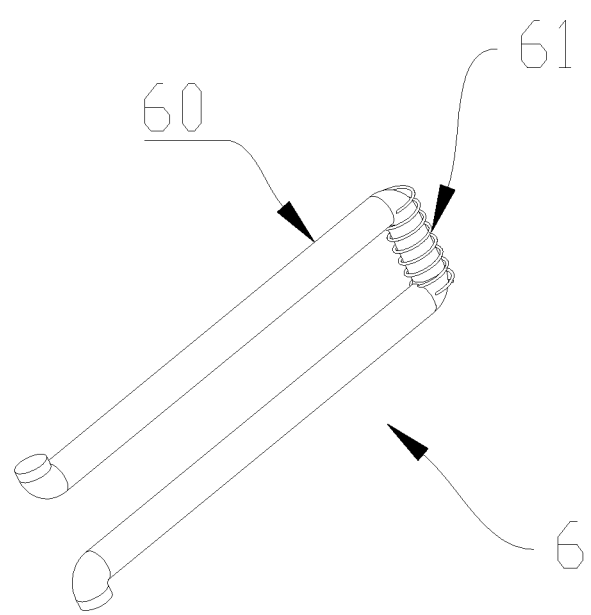
FIG. 12 is a perspective view of a heating element of the atomization assembly shown in FIG. 3.

Referring to FIG. 12, the heating element 6 comprises a wick 60 and a heater coil 61. The wick 60 runs through the snorkel 7 radially, and the heater coil 61 is positioned in the snorkel 7, with the wick 60 extending therethrough. The two ends of the wick 60 extend toward the first connector 10 vertically along the side wall of the snorkel 7. And the two ends of the heater coil 61 are electrically connected to the first connector 10 and the second connector 12 respectively. One end of the heater coil 61 is connected to an electronic wire. One end of the electronic wire, away from the heater coil 61 is champed between the inner surface of the atomization base 8 and the second connector 12, so that the heater coil 61 is electrically connected to the second connector 12 via the electronic wire. And the other end of the heater coil 61 is electrically connected to the first connector 10 via the electrical contact with the fixed tube 5. The tobacco oil stored in the oil storage cavity 33 permeates into the wick 60 via the oil outlet 50 defined in the side wall of the fixed tube 5, and the heater coil 61 is configured to atomize the tobacco oil permeated into the wick 60. In order to obtain easier outflow for the tobacco oil, the oil outlet 50 is defined on the side wall of the fixed tube 5, wherein the side wall of the fixed tube 5 is close to the first connector 10, so it ensures that the tobacco oil can smoothly permeate into the wick 60 via the oil outlet 50 even when there is less tobacco oil in the oil storage cavity 33.

In the present embodiment, the tobacco oil is stored in the oil storage cavity 33 of the atomization assembly, and the tobacco oil is added into the storage cavity 33 through the filler hole 31 defined in the open end 30 of the body 3. The mouthpiece 1 has no direct contact with the storage cavity 33, therefore, on the premise that the filler hole 31 is sealed up by the elastomeric seal 2, the tobacco oil leakage between the mouthpiece 1 and the storage cavity 33 can be avoid effectively. Further, it is more convenient to add the tobacco oil. The mouthpiece 1 will not contaminated with the tobacco oil when it is removed, therefore it will not affect the taste of the smoke. In addition, the atomization unit of the present embodiment is accommodated in the fixed tube 5, which makes the storage cavity 33 has a greater volume and a larger reservoir respectively, thus the tobacco oil can be filled up to improve the user experiences. Meanwhile, the atomization unit in the present embodiment is provided with compact structure, easy assembly and space saving.

In addition, the present application further provides an electronic cigarette comprising an atomization assembly and a battery assembly configured to provide electricity supply for the atomization assembly, and the atomization assembly of the electronic cigarette has any of the structural features as above-mentioned, so there is no need to repeat here. In order to obtain an effective electrical connection between the atomization assembly and the battery assembly, in the atomization assembly, a connection part is defined at one end of the first connector 10, wherein the end of the first connector points to the battery assembly, and the connection part is formed by reducing the diameter of the first connector 10. An external thread is defined on the outer peripheral surface of the connection part. An internal thread adapted to the external thread of the first connector 10 is defined inside a connection end of the battery assembly, and the connection end is connected to the atomization assembly. The atomization assembly and the battery assembly are fixed by a threaded connection between the connection end of the battery assembly and the first connector 10, and the threaded connection further ensures that the first connector 10 is effectively electrically connected to the battery assembly. It should be understand that the connection between the battery assembly and the atomization assembly is not limited to the threaded connection as described above, and the connection can be an up tight fit connection, a snap-fit connection or a magnetic connection and the like, which is not limited here.

In addition, the present application further provides a method for assembling an electronic cigarette, the electronic cigarette comprises an atomization assembly and a battery assembly, and the atomization assembly has any of the technical features of the atomization assembly described above, so there is no need to repeat here. The method comprises the following steps:

a. a step for adding the tobacco oil: adding the tobacco oil to the oil storage cavity 33 via the filler hole 31 that is defined on the bottom wall of the receiving groove 34. As the filler hole 31 is defined on the bottom wall of the receiving groove 34 defined at the open end 30 of the body 3, when adding the tobacco oil, the tobacco oil is injected directly by aligning the filler hole 31 via the receiving groove 34 exposed from the open end 30 of the body 3, and the tobacco oil directly flows to the oil storage cavity 33 that is used for storing the tobacco oil in the body 3.

b. a step for sealing: inserting the elastomeric seal 2 into the receiving groove 34 to seal up the filler hole 31. When the tobacco oil is filled, inserting the elastomeric seal 2 into the receiving groove 34 can seal up the filler hole 31 and avoid the tobacco oil leaking out from the filler hole 31. The elastomeric seal 2 in the present embodiment is a seal cover, and the shape of the seal cover is adapted to the receiving groove 34. Therefore, the side wall of the elastomeric seal 2 will elastically abut against the side wall of the receiving groove 34 after the elastomeric seal 2 is fastening with the receiving groove 34, which will enhance the sealing effect of the elastomeric seal 2 to the filler hole 31. In other non-limiting embodiments, it is workable to insert the elastomeric seal 2 into the filler hole 31 directly to seal up the filler hole 31, if the shape of the elastomeric seal 2 is just adapted to the filler hole 31.

c. a step for electrical connecting: connecting the atomization assembly to the battery assembly and making the atomization assembly electrical connected to the battery assembly. The way the atomization assembly connected to the battery assembly in the present embodiment is a threaded connection, so an internal thread adapted to an external thread of the connection end of the first connector 10 is defined on the battery assembly, and the atomization assembly and the battery assembly are connected by the threaded connection between the battery assembly and the first connector 10. It should be understand that the way the atomization assembly connected to the battery assembly in the present embodiment is not limited to above threaded connection, and can also be a magnetic connection or a snap-fit connection and the like.

In conclusion, in the atomization assembly, electronic cigarette and the method for assembling the electronic cigarette of the present application, by means of arranging a receiving groove 34 at the open end 30 of the body 3, and defining an filler hole connected to the oil storage cavity 33 on the bottom wall of the receiving groove 34, firstly, the tobacco oil will be injected into the oil storage cavity 33 via the filler hole 31 directly just by removing the mouthpiece 1 from the open end 30 when adding the tobacco oil during which the tobacco oil will not be leaked out; and then the filler hole 31 can be sealed up by the elastomeric seal 2 after the tobacco oil is added; lastly, the mouthpiece 1 can be assembled to the open end 30 to prevent the open end 30 from being contaminated with the tobacco oil. Therefore, it is much cleaner. Meanwhile, as the filler hole 31 is sealed up by the elastomeric seal 2 during used, and it is able to effectively avoid the tobacco oil between the oil storage cavity 33 and the mouthpiece 1 leaking out.

The embodiments of the present application have been described accompanying with the drawings, while the present application is not limit to the aforementioned specific

The invention claimed is:

1. An atomization assembly configured to be combined with a battery assembly to form an electronic cigarette, comprising a mouthpiece (1) and a body (3) detachable with the mouthpiece (1), wherein the body (3) includes an open end (30) that is configured to discharge smoke into the mouthpiece (1), an oil storage cavity (33) configured to store tobacco oil is defined inside the body (3), a receiving groove (34) is defined at the open end (30), a filler hole (31) connected to the oil storage cavity (33) is defined on a bottom wall of the receiving groove (34), and an elastomeric seal (2) configured to seal up the filler hole (31) is received in the receiving groove (34).

2. The atomization assembly of claim 1, wherein, the elastomeric seal (2) is inserted into the filler hole (31) and is elastically abutted against an inner wall of the filler hole (31).

3. The atomization assembly of claim 1, wherein, one end of the elastomeric seal (2) is abutted against the receiving groove (34), and the other end of the elastomeric seal (2) is abutted against the mouthpiece (1).

4. The atomization assembly of claim 3, wherein, the elastomeric seal (2) includes a through hole (24) that is configured to discharge the smoke into the mouthpiece (1).

5. The atomization assembly of claim 4, wherein, a first convex (21) abutted against a side wall of the receiving groove (34) is defined outwardly on an outer wall of the elastomeric seal (2) and in a radial direction of the elastomeric seal (2).

6. The atomization assembly of claim 4, wherein, a receiving cavity configured to accommodate an atomization unit is formed inside the body (3), the atomization unit is configured to atomize the tobacco oil stored in the oil storage cavity (33) and produce the smoke, a connection tube (32) extends from the bottom wall of the receiving groove (34) to the inside the receiving cavity and is configured to guide the smoke flowing to the through hole (24), and the connection tube (32) is connected to the through hole (24).

7. The atomization assembly of claim 6, wherein, one end of the connection tube (32), away from the atomization unit, extends to the inside the receiving groove (34), an inner cavity (25) configured to accommodate a part of the connection tube (32) is defined inside the elastomeric seal (2), and the inner cavity (25) is connected to the through hole (24).

8. The atomization assembly of claim 7, wherein, a second convex (22) abutted against a side wall of the connection tube (32) is defined inwardly on a side wall of the inner cavity (25) and in a radial direction of the inner cavity (25).

9. The atomization assembly of claim 6, wherein, a fixed tube (5) configured to receive the atomization unit is defined at one end of the connection tube (32), the end of the connection tube (32) is away from the open end (30); a first connector (10) is defined at one end of the fixed tube (5), the end of the fixed tube (5) is away from the connection tube (32), the first connector (10) is configured to avoid the tobacco oil leaking to the outside of the body (3), an outer wall of the first connector (10) abuts against an inner wall of the body (3), and an outer wall of the fixed tube (5), the inner wall of the body (3) and the first connector (10) are enclosed to form the oil storage cavity (33).

10. The atomization assembly of claim 9, wherein, an oil outlet (50) is defined on a side wall of the fixed tube (5), the side wall of the fixed tube (5) is close to a bottom of the oil storage cavity (33), and the oil outlet (50) is configured to guide the tobacco oil stored in the oil storage cavity (33) flowing to the atomization unit.

11. The atomization assembly of claim 9, wherein, a connection sleeve (4) is arranged between the fixed tube (5) and the connection tube (32), and the connection sleeve (4) is configured to avoid the tobacco oil permeating to the connection tube (32).

12. The atomization assembly of claim 11, wherein, the connection sleeve (4), the connection tube (32) and the fixed tube (5) are coaxially arranged, and a first slot (41) into which the fixed tube (5) is inserted is defined in the connection sleeve (4).

13. The atomization assembly of claim 12, wherein, a second slot (40) is configured to accommodate and abut against the connection tube (32) is defined in the connection sleeve (4), and the connection tube (32), the connection sleeve (4) and the fixed tube (5) are axially connected to each other.

14. The atomization assembly of claim 13, wherein, a third convex (42) abutted against the connection tube (32) is defined inwardly on the inner wall of the second slot (40) and in a radial direction of the second slot (40).

15. The atomization assembly of claim 1, wherein, the open end (30) includes a first threaded portion (200) that is integrated with the body (3), a second threaded portion (100) adapted to the first threaded portion (200) is defined at one end of the mouthpiece (1), the end of the mouthpiece (1) is close to the open end (30), and the mouthpiece (1) is detachably connected to the body (3) via the connection between the first threaded portion (200) and the second threaded portion.

16. The atomization assembly of claim 15, wherein, the first threaded portion (200) comprises a connection part and a first thread defined on an outer peripheral surface of the connection part, and the connection part is formed by reducing a diameter of the open end (30) by the body (3); and the second threaded portion (100) comprises a second thread, the second thread is defined on an inner peripheral surface of the mouthpiece (1) and is adapted to the first thread.

17. The atomization assembly of claim 16, wherein, a fourth convex (23) abutted against the second thread is defined at one end of the elastomeric seal (2) and the end of the elastomeric seal (2) is close to the mouthpiece (1).

18. An electronic cigarette comprising an atomization assembly and a battery assembly configured to provide electricity supply for the atomization assembly, wherein, the atomization assembly is the atomization assembly of claim 1.

19. A method for assembling an electronic cigarette, the electronic cigarette comprises an atomization assembly and a battery assembly, wherein, the atomization assembly is the atomization assembly of claim 1, and the method comprises the following steps:

a. a step for adding the tobacco oil: adding the tobacco oil to the oil storage cavity (33) via the filler hole (31) that is defined on the bottom wall of the receiving groove (34);

b. a step for sealing: inserting the elastomeric seal (2) into the receiving groove (34) to seal up the filler hole (31);

c. a step for electrical connecting: connecting the atomization assembly to the battery assembly, and making the atomization assembly be electrical connected to the battery assembly.

* * * * *